United States Patent
Vitti (10) Patent No.: US 12,121,861 B2
(45) Date of Patent: Oct. 22, 2024

(54) METHOD AND SYSTEM FOR ISOLATION OF MESENCHYMAL STEM CELL EXOSOMES

(71) Applicant: AVAV LABS LLC, Lee's Summit, MO (US)

(72) Inventor: Philipp R. Vitti, Kansas City, MO (US)

(73) Assignee: AVAV Labs LLC, Lee's Summit, MO (US)

( * ) Notice: Subject to any disclaimer, the term of this patent is extended or adjusted under 35 U.S.C. 154(b) by 854 days.

(21) Appl. No.: 17/085,695

(22) Filed: Oct. 30, 2020

(65) Prior Publication Data

US 2022/0133803 A1    May 5, 2022

(51) Int. Cl.
| | |
|---|---|
| *B01D 63/02* | (2006.01) |
| *A61K 35/28* | (2015.01) |
| *B01D 39/16* | (2006.01) |
| *B01D 61/14* | (2006.01) |
| *B01D 69/02* | (2006.01) |
| *B01D 69/08* | (2006.01) |
| *B01D 71/68* | (2006.01) |

(52) U.S. Cl.
CPC ............. *B01D 63/02* (2013.01); *A61K 35/28* (2013.01); *B01D 39/16* (2013.01); *B01D 61/147* (2013.01); *B01D 69/02* (2013.01); *B01D 69/08* (2013.01); *B01D 71/68* (2013.01); *B01D 2239/1216* (2013.01); *B01D 2311/2649* (2013.01); *B01D 2313/243* (2013.01); *B01D 2315/16* (2013.01); *B01D 2317/025* (2013.01); *B01D 2325/02834* (2022.08)

(58) Field of Classification Search
None
See application file for complete search history.

(56) References Cited

U.S. PATENT DOCUMENTS

| | | | |
|---|---|---|---|
| 10,538,727 B2* | 1/2020 | Bransby | B01D 71/26 |
| 2004/0185041 A1* | 9/2004 | Walker | A61M 1/3468 424/140.1 |
| 2009/0287021 A1* | 11/2009 | Hathaway, Jr. | B01J 19/1881 422/224 |
| 2010/0326928 A1* | 12/2010 | Osterhoudt | B01D 29/58 210/485 |

OTHER PUBLICATIONS

Kim et al. "Cyclic tangential flow filtration system for isolation of extracellular vesicles" (2021), APL Bioengineering, vol. 5, 016103, 1-10. (Year: 2021).*

Haraszti, R.A. et al.(Exosomes Produced from 3D Cultures of MSCs by Tangential Flow Filtration Show Higher Yield and Improved Activity, Molecular Therapy, vol. 26 No 12: 2838-2847, 2018, https://www.cell.com/molecular-therapy-family/molecular-therapy/pdfExtended/S1525-0016(18)30456-8 (Year: 2018).*

(Continued)

*Primary Examiner* — Matthew D Krcha
*Assistant Examiner* — Brittany I Fisher
(74) *Attorney, Agent, or Firm* — Polsinelli PC (57) ABSTRACT

Disclosed is a system and method for isolating large quantities of viable, undamaged exosomes from liquid, cell-free mesenchymal stem cell cultures using tangential flow filtration.

39 Claims, 9 Drawing Sheets

(56) References Cited

OTHER PUBLICATIONS

Alvarez, M.L. et al., "Comparison of protein, microRNA, and mRNA yields using different methods of urinary exosome isolation for the discovery of kidney disease biomarkers", *Kidney International*, 82(9):1024-1032, 2012, https://doi.org/10.1038/ki.2012.256.

Contreras-Naranjo, J.C. et al., "Microfluidics for exosome isolation and analysis: enabling liquid biopsy for personalized medicine", *Lab on a Chip*, 17(21):3558-3577, 2017, https://doi.org/10.1039/C7LC00592J.

Liang, K. et al., "Nanoplasmonic quantification of tumour-derived extracellular vesicles in plasma microsamples for diagnosis and treatment monitoring", *Nature Biomedical Engineering*, 1(4):0021, 2017, https://doi.org/10.1038/s41551-016-0021.

Livshits M.A. et al., "Isolation of exosomes by differential centrifugation: Theoretical analysis of a commonly used protocol", *Scientific Reports*, 5(1):17319, 2015, https://doi.org/10.1038/srep17319.

Patel, G.K. et al., "Comparative analysis of exosome isolation methods using culture supernatant for optimum yield, purity and downstream applications", *Scientific Reports*, 9(1):5335, 2019, https://doi.org/10.1038/s41598-019-41800-2.

Yu, L.L. et al., "A Comparison of Traditional and Novel Methods for the Separation of Exosomes from Human Samples", *BioMed Research International*, 1-9, 2018, https://doi.org/10.1155/2018/3634563.

Webpage https://www.technologynetworks.com/cellscience.

\* cited by examiner

METHOD AND SYSTEM FOR ISOLATION OF MESENCHYMAL STEM CELL EXOSOMES

FIELD OF THE INVENTION

The present invention is in the field of therapeutic biologics production. Moore particularly, the invention relates to systems and methods for the provision of therapeutic exosomal products.

BACKGROUND

Mesenchymal stem cells (MSCs) are highly proliferative, multipotent cells that can be isolated from a number of tissues including umbilical cord, placenta, bone marrow, and fat and can differentiate into mesenchymal cell types, with negligible risk of teratoma formation. These cells secrete exosomes which are lipid microparticles or vesicles of about 30 mm to −100 mm in diameter. Exosomes carry protein, lipid, and RNA loads from the cell, and as such, perform a functional role that mediates cellular-cell communication and cellular immunity. They are also thought to play a role as biomarkers of certain neurological disorders. Because exosomes are a form of "natural" drug delivery, and do not elicit acute immune rejection, they have been loaded ex vivo with certain therapeutic agents and targeted to deliver their therapeutic loads to specific cells types.

Exosomes have been obtained by a number of different methods, including ultracentrifugation and density gradient ultracentrifugation. Other methods incudes ultrafiltration by centrifugation through a centrifugal concentrator (e.g., Vivaspin 6 Centrifugal Concentrator (100 k MWCO, Satorius, Goettingen, Germany), polymer-based precipitation methods (e.g., using a Total Exosome Isolation kit, Invitrogen, MA, USA), by polymer-based precipitation with size-based purification (e.g., Exo-Spin™ Exosome Purification Kit, Cell Guidance Systems, Cambridge, UK), exclusion chromatography, and by column filtration). Other exosome isolation methods rely on immunophenotype-based enrichment of the exosome sample, which requires antibodies to bind with surface proteins on the xosome.[2] The antibodies can be linked to beads, which enable density-based isolation of bead-bound exosomes. Yet another method uses chemically modified membranes chemically modified to have an increased surface area conjugated to a lectin-based EV-binding compound which can be assembled into benchtop centrifuge-compatible spin columns.

Many of these methods suffer from several disadvantages. For example, because exosomes can be damaged at high centrifugal speeds, and additional debris and larger-sized particles can be pulled down during isolation, ultracentrifugation-based preparations can result in decreased yields and result in a heterologous collection of exosomes and debris. As such, as concentration thresholds are required for them to be therapeutic, it is difficult to obtain enough via ultracentrifugation methods to approach that threshold. Also, centrifugal methods often require large volumes, and removing the supernatant without disturbing the small exosomal pellet can be technically challenging and difficult to replicate (Jeppesen 2014).

Another problem relates to the heterogenic nature of exosomes sometimes obtained from mesenchymal stem cells, leading to the possibility that subtypes of populations of the cells and their exosomes having different potentials are present in the isolate fraction. Antibody-based affinity methods and density gradient centrifugation although capable of purifying highly purified exosomes, are incapable of yielding a high percentage of intact exosomes, making it difficult to characterize the physiological functions. Other isolation methods, such as polymer precipitation using commercially available kits, has been shown to yield exosome preparations with large amounts of contaminants that seriously interfere with subsequent experiments.

Thus, methods of obtaining preparations of exosomes that are homogenous, intact, free of contaminants, and concentrated enough to provide commercially viable and therapeutic yields are still needed.

SUMMARY

It has been discovered that exosomes obtained from the cell free culture medium of mesenchymal stem cells cultured from human umbilical cord tissue can be isolated and concentrated using a downstream processing method including tangential flow filtration. It has also been discovered that the exosomes isolated by this process are substantially undamaged, of high yield, free of debris and contaminants, and of therapeutic use-quality. These discoveries have been exploited to provide the present disclosure, which at least in part is directed to a method and system for isolating human mesenchymal stem cell exosomes.

In one aspect, the disclosure provides a method of isolating a plurality of substantially undamaged exosomes from a liquid culture of mesenchymal stem cells (MSCs). The method comprises: removing the MSCs from the liquid culture to obtain a liquid cell-free culture medium; and isolating the plurality of exosomes from the liquid cell-free culture medium by tangential flow filtration.

In some embodiments, the plurality of exosomes is isolated from the liquid cell-free culture medium by: filtering the liquid cell-free culture medium through a first hollow fiber filter having a pore size of about 0.1 μm to about 1.0 μm to obtain a first permeate; and subjecting the first permeate to diafiltration through a second hollow fiber filter having a pore size of about 30 kD to 600 kD to obtain a retentate. In some embodiments, the hollow fiber filter comprises polysulfane, polysulfone, and/or modified polysulfone.

In certain embodiments, the first hollow fiber filter has a pore size of about 0.65 μm. In some embodiments, the second hollow fiber filter has a pore size of about 30 kD to about 150 kD, or about 100 kD.

In particular embodiments, the method further comprises filtering the first permeate through an intermediate hollow fiber filter having a pore size of about 0.45 μm to about 2.0 μm, to obtain a second permeate, and then filtering the second permeate through the second hollow fiber to obtain the permeate. In specific embodiments, the intermediate hollow fiber filter has a pore size of about 0.1 μm.

In some embodiments, the MSC culture is obtained from human placental and/or umbilical cord tissue.

In certain embodiments, the MSCs are removed from the mesenchymal stem cell culture by gravity filtration, and in particular embodiments, the MSCs are removed by filtration through at least one filter having a pore size of at least about 0.4 μm. In some embodiments, the prefilter(s) comprise(s) polypropylene.

In some embodiments, the retentate consists essentially of a plurality of exosomes, and in specific embodiments, about 32 trillion to about 50 trillion exosomes are obtained from a culture of about 7 billion to about 10 billion MSCs using the method of the disclosure.

In another aspect, the disclosure provides a system for the production of a plurality of exosomes. The method comprises: a source of liquid cell-free culture medium from a liquid mesenchymal stem cell (MSC) culture; a first tangential flow filter (TFF) for separating the cell-free culture medium into a first permeate and a first retentate; and a second TFF in fluid communication with the first TFF for separating the first permeate into a second permeate and a second retentate, wherein the second retentate comprises the plurality of exosomes.

In some embodiments, the first TFF is a hollow fiber filter having a pore size of about 0.1 µm to about 1.0 µm. In certain embodiments, the second TFF is a hollow fiber filter having a pore size of about 30 kD to about 600 kD or 60 kD to about 150 kD. In a particular embodiment, the first TFF has a pore size of about 0.65 µm, and in some embodiments, the second TFF has a pore size of about 100 kD.

In some embodiments, the system further comprises: an intermediate TFF in fluid communication with, and intermediate, the first TFF and the second TFF; an input of the intermediate TFF being in fluid communication with a permeate output of the first TFF; and a retentate output of the intermediate TFF being in fluid communication with an input of the second TFF. In specific embodiments, the intermediate TFF has a pore size of about 0.45 µm to about 2.0 µm, or about 0.1 µm. In some embodiments, the first and second TFFs are comprised of polysulfane, polysulfone, and/or modified polysulfone.

In certain embodiments, the system further comprises a prefilter module through which the liquid MSC culture medium is passed to obtain the source of liquid, cell-free MSC culture medium. In some embodiments, the prefilter module pore size is between about 10.0 µm and about 0.1 µm. In particular embodiments, the prefilter module comprises a sequence of plural, discrete prefilters, each having a successively smaller filter pore size. In some embodiments, the sequence of plural discrete filters is comprised of three successive discrete prefilters having filter pore sizes of about 8.0 µm, about 0.8 µm, and about 0.45 µm, respectively. In certain embodiments, each of the plural discrete prefilters comprise polypropylene.

In some embodiments, the system further comprises a first feed vessel in fluid communication with the prefilter module and the first TFF. In particular embodiments, the system further comprises a first feed vessel in fluid communication with the liquid, cell-free culture medium source and the first TFF, the first feed vessel configured to receive the liquid, cell-free culture medium and to provide the liquid, cell-free culture medium to the first TFF. In some embodiments, the first feed vessel is further configured to receive the retentate from a retentate output of the first TFF and to return the retentate from the first TFF to an input of the first TFF. In other embodiments, the system further comprises a first pump intermediate the first feed vessel and the first TFF for selectively pumping the contents of the first feed vessel to an input of the first TFF.

In some embodiments, the system further comprising a second feed vessel in fluid communication with a permeate output of the first TFF and an input of the second TFF, the second feed vessel configured to receive permeate from a permeate output of the first TFF and to provide the first TFF permeate to an input of the second TFF. In some embodiments, the system further comprises second pump intermediate and in fluid communication with the permeate output of the first TFF and the second feed vessel for selectively pumping the permeate of the first TFF to the second feed vessel. In addition, in some embodiments, the system further comprises a third pump intermediate and in fluid communication with the second feed vessel and the input of the second TFF for selectively pumping the contents of the second feed vessel to an input of the second TFF.

In some embodiments, the second feed vessel is configured to receive the retentate from a retentate output of the second TFF and to return the retentate from the second TFF to the input of the second TFF. In particular embodiments, the system further comprises a diafiltration reservoir in fluid communication with the second feed vessel for providing a supply of diafiltration buffer thereto, whereby the second feed vessel is configured to provide diafiltration buffer to the input of the second TFF.

In some embodiments, the system further comprises a fourth pump intermediate and in fluid communication with the diafiltration reservoir and the second feed vessel for selectively pumping the contents of the diafiltration reservoir to the second feed vessel. The system can further comprise a product reservoir in fluid communication with a retentate output of the second TFF for selectively receiving the retentate therefrom, the retentate from the second TFF comprising the plurality of exosomes.

DESCRIPTION OF THE DRAWING

The foregoing and other objects of the present disclosure, the various features thereof, as well as the disclosure itself may be more fully understood from the following description, when read together with the accompanying drawings in which.

DESCRIPTION

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated or caused by the state, disorder or disease being treated. In certain embodiments, the treatment comprises bringing into contact with an infection an effective amount of an anti-infective formulation of the disclosure for conditions related to infections.

As used herein, the term "patient," "individual," or "subject" refers to a human or a non-human mammal. Non-human mammals include, but are not limited to, livestock and pets, such as ovine, bovine, porcine, canine, feline, lupine, murine, and marine mammals.

As used herein, the terms "effective amount," "pharmaceutically effective amount," and "therapeutically effective amount" refer to a nontoxic but sufficient amount of the purine, purine precursor, purine analog, pyrimidine, pyrimidine precursor, and/or pyrimidine analog to provide the desired biological result. That result may be reduction or alleviation of the signs, symptoms, or causes of a disease, e.g., cancer, or any other desired alteration of a biological system. An appropriate therapeutic amount in any individual case may be determined by one of ordinary skill in the art using routine experimentation.

The term "comprising" encompasses the term "including".

The terms "culture", "culture medium", "cell culture", and "MSC culture" as used herein refer to a mesenchymal stem cell population that is suspended in a medium under conditions suitable to survival and/or growth of the cell population. These terms as used herein refer to the combination comprising the MSC population and the medium in which the population is suspended.

The terms "medium", "media", "culture medium", and "growth medium" as used herein refer to a substance containing components to support living cells, e.g., nutrients which nourish growing MSCs (i.e., a growth medium), and/or which supports the collection of cells from their expansion or maintenance container (e.g., a collection medium). Typically, these media provide essential and non-essential amino acids, vitamins, energy sources, lipids, and trace elements required by the cell for minimal growth and/or survival. A growth medium can also contain components that enhance growth and/or survival above the minimal rate, including hormones and growth factors. Media are formulated to a pH and salt concentration optimal for cell survival and proliferation. The medium may take any form, such as a solid (as in a petri dish), or liquid.

As used herein, the term "filtrate" refers to the solution and its contents that have passed through a filter.

As used herein, the term "permeate" refers to the solution and its contents that have passed through a membrane filter.

As used herein, the term "retentate" encompasses the components of a solution that have not passed through, and thus are retained by, a membrane filter.

The term "hollow fiber filter (or HFF) as used herein refers to tubes, cassettes, packs, and any container known in the art to contain and comprise hollow fiber filters.

The term "diafiltration" as used herein encompasses a dilution process that involves removal or separation of permeable components ("permeates") from a solution based on their molecular size with micro-molecule permeable filters in order to obtain a more pure solution. For example, to effectively remove permeate components from solution, fresh solvent may be added to the feed to replace the permeate volume, at the same rate as the permeate flow rate, such that the volume in the system remains constant.

"Tangential flow filtration" (TFF) is a type of filtration in which the majority of the feed flow travels tangentially across the surface of a filter, rather than into the filter. This type of filtration is useful for feeds containing a high proportion of small particle size solids (where the permeate is the product) because solid material can quickly block (blind) the filter surface with dead-end filtration. The term "TFF" also encompasses the filtration device which can be a tube, cassette or any container that comprises one or more hollow fiber filter(s).

The term "prefilter" as used herein is a preliminary filtering element, module, device, or process step or steps used upstream of a membrane filter in order to remove relatively large particulates and to reduce the pressure drop when filtering through one or more downstream membrane filters. The size of the housing needed for downstream membrane filters may thus be reduced.

The present disclosure provides a method of isolating a large number of undamaged exosomes suitable for therapeutic use from the medium of a liquid mesenchymal stem cell culture, and a system for obtaining the same. This method uses tangential flow filtration to obtain and concentrate the exosomes produced by MSCs and excreted into their medium.

Isolation Method

The present method provides substantially undamaged and pure exosomes isolated from a liquid culture of human mesenchymal stem cells. One simplified example of this method is summarized in FIG. 1. It is understood that this simplified flow chart may not explicitly list every step useful for obtaining an exosome product.

The MSC culture may be derived from explants of adult and embryonic tissues, such as adipose tissue, muscle, peripheral blood, lung, heart, corneal stroma, dental pulp, placenta, umbilical cord, endometrium, amniotic membrane, and Wharton's jelly, by any method known in the art. For example, MSCs can be obtained from explants of human placental or umbilical cord tissue according to the method of Wu et al (*Scientific Reports* (2018) 8:5014). Some exemplary useful MSC tissue sources include umbilical cord, as MSCs from this tissue have similar immune phenotype and multilineage differentiation, but higher expansion potential relative to bone marrow MSCs and adipose-derived MSCs, and Wharton's jelly. Wharton's jelly (substantia gelatinea funiculi *umbilicalis*), a gelatinous substance within the umbilical cord, derived from extra-embryonic mesoderm, can be commercially obtained, and MSCs can be isolated from it via e.g., the enzymatic, enzymatic-explant, and explant methods (see. e.g., Vara I (2019) *Iran J. Med Sci.* 44(6):437-448).

Liquid MSC cultures of any size can be produced by expanding the original MSC source in a growth medium to any volume which will provide a useful number of exosomes.

The MSCs are removed from the liquid culture by any method known in the art, such as, but not limited to, by centrifugation, gravity filtration, density filtration, syringe filtration, vacuum filtration, column filtration, column chromatography, etc.

For example, the MSCs can be removed from the culture medium by gravity filtration through a prefilter having a pore size of at least 0.4 μm, e.g., about 0.4 μm to about 10 μm. The prefilter can be in the form of a module comprising one or more individual prefilters. For example, the MSC culture medium can be subjected to filtration through a gravity prefilter module comprising a prefilter having a pore size of about 100 μm, followed by a series of prefilters with decreasing pore size, such as a prefilter having a pore size of at least about 0.4 μm, such as about 8.0 μm, about 0.8 μm, and/or about 0.45 μm. These prefilters can be made of any commercially available or other material with the desired pore size, and which does not have any attractive or repulsive characteristics. One nonlimiting, useful prefilter material comprises polypropylene.

The cell-free medium is then processed by tangential flow filtration to obtain the exosomes produced and secreted in the culture medium by the MSCs before the cells are removed from the liquid culture medium. Exosome collection is accomplished by filtering the cell-free culture medium through a commercially obtainable first hollow fiber filter having a pore size of about 0.1 μm to about 1.0 μm to obtain a permeate. For example, the hollow fiber filter may be a hollow fiber filter having a pore size of about 0.1 μm, about 0.1 μm, about 0.2 μm, about 0.3 μm, about 0.4 μm, about 0.5 μm, about 0.6 μm, about 0.65 μm, about 0.7 μm, about 0.8 μm, about 0.9 μm, or 1.0 μm.

The permeate of the first hollow fiber filter is then subjected to diafiltration through a hollow fiber filter having a pore size of about 30 kD to about 600 kD, about 60 kD to about 600 kD, about 40 kD to about 150 kD, about 60 kD to about 150 kD to obtain a retentate which contains the exosomes. For example, the permeate may be subjected to diafiltration through a second hollow fiber filter tube having a pore size of about 30 kD, about 40 kD, about 50 kD, about 60 kD, about 70 kD, about 80 kD, about 90 kD, about 100 kD, about 110 kD, about 120 kD, about 130 kD, about 140 kD, about 150 kD, about 200 kD, about 250 kD, about 300 kD, about 350 kD, about 400 kD, about 450 kD, about 500 kD, or about 600 kD.

Optionally, the permeate from the first hollow fiber filter may be filtered through an intermediate hollow fiber filter tube have a pore size of about 0.45 μm to about 2.0 μm, about 0.5 μm, about 0.6 μm, about 0.70 μm, about 0.8 μm, about 0.9 μm, about 1.0 μm, about 1.1 μm, about 1.2 μm, about 1.3 μm, about 1.4 μm, about 1.5 μm, about 1.6 μm, about 1.70 μm, about 1.8 μm, about 1.9 μm, or about 2.0 μm to obtain a second permeate which is then subjected to diafiltration through the second hollow fiber filter.

These hollow fiber filters may be in any form, such as, but not limited to, a tube or cassette. These filters comprise polysulfane, polysulfone, and/or "modified" polysulfone, such as, but not limited to, polyethersulfone (see, e.g., (Repligen, Waltham, MA) or the addition of amine and/or sulfonyl groups. The final retentate from the second hollow fiber filter comprises or consists substantially of, the collected exosomes.

The amount or yield of exosomes in the retentate can be estimated as follows: A single MSC produces about 1,000 to about 2,200 exosomes per day in a typical MSC growth medium Thus about $3 \times 10^9$ can be obtained from a 15 liter bioreactor MSC culture. For commercial purposes, a useful amount of MSCs are grown to provide a sufficient number of exosome from which a therapeutic product can be made. The present method provides a yield of about 32 trillion to about 50 trillion exosomes from a culture of about 7 billion to about 10 billion mesenchymal stem cells. For example, about 42 trillion exosomes can be expected to be secreted and harvested from about $9 \times 10^9$ MSCs. In another example, from about $10 \times 10^6$ MSCs from an umbilical cord sample, expanded to about $9 \times 10^6$ MSCs secrete into the cell medium of the bioreactor about $42 \times 10^{12}$ exosomes before the isolation procedure is initiated.

A dissected sample of the umbilical cord tissue which will be used to obtain MSC exosomes was examined by flow cytometry to see what type of cells were in the sample. This method validates the identity of the cells by detecting the expression of certain expected enzymatic and other antigenic markers on the MSC surface. The dissected tissue sample was then cultured and expanded in a growth medium. A sample of the expanded cell culture medium was then subjected to flow cytometry and examined for the expression of certain MSC surface markers to determine the identity of the cells in the culture. The results, shown in FIG. 2A-2G demonstrate that the expanded cells are MSCs. An exosomal sample from the retentate obtained from this MSC sample was also examined to determined is the exosomes from these MSCs expressed certain expected MSC markers (CD20, CD34, CD45, CD73, CD90, CD105, CD166, and HLA-DR). The results shown in FIGS. 3A-3I indicate that the exosomes do express these markers and thus are viable.

That the MSC exosomes isolated by the present method and system are substantially undamaged and pure can be determined by any exosomal characterization method known in the art, e.g., nanoparticle tracking analysis, exosomal surface marker-based characterization by flow cytometry, fluorescence-activated cell sorting (FACS), Western blotting, enzyme-linked immunosorbent assay (ELISA), MA-based characterization, Tunable Resistance Pulse Sensing (TRPS) characterization. At least some of these methods track the presence of the markers such as CD20, CD34, CD45, CD73, CD90, CD105, CD166, and HLA-DR expected to be on viable exosomes.

Exosome yield can be determined from a sample of the retentate by any method known in the art (see, Koritzinsky (2017) *J. Cell Physiol.* 232(7):1587-1590), e.g., by particle counting systems such as Izon qEV and TRPS systems, Nanosight's Nanoparticle's Nanoparticle Tracking Analysis, Tunable Resistive Pulse Sensing, by vesicle flow cytometry, Surface Plasmon resonance, or by electron microscopy.

Exosomal Isolation System

The present disclosure also provides a system for obtaining a plurality of exosomes from a source of cell-free MSC culture medium. As disclosed herein, exosomes can be obtained from a cell-free liquid MSC culture by the method and using the system of the present disclosure.

In general, the system comprises a first tangential flow filter (TFF) 236 in communication with the source of cell-free culture medium 230. Such a first TFF is shown in FIG. 4C and is discussed in the context of an illustrative embodiment in greater detail below. The first TFF generates a retentate and a permeate. The system further comprises a second TFF 256, such as shown in FIG. 4D. The input of the second TFF is in direct or indirect fluid communication with the permeate of the first TFF. The second TFF also generates a retentate and a permeate, the latter comprising the plurality of exosomes.

As discussed subsequently, a first embodiment of the first TFF 236 is selected to have a pore size of about 0.1 μm to about 1.0 μm, and a particular embodiment of the first TFF may have a pore size of about 0.65 μm. Other pore sizes are employable with respect to the first TFF.

Also, as discussed subsequently, a first embodiment of the second TFF 256 is selected to have a pore size of about 30 kD to about 600 kD, and a particular embodiment of the second TFF may have a pore size of about 100 kD. Other pore sizes are employable with respect to the second TFF.

Optionally, the presently disclosed system may additionally comprise an intermediate TFF 262. An input of the intermediate TFF may be in direct or indirect fluid communication with a permeate output of the first TFF 236 and a retentate output of the intermediate TFF may be in direct or indirect fluid communication with the input of the second TFF 256. As discussed subsequently, this intermediate TFF, if employed, may have a pore size of about 0.45 μm to about 2.0 μm. In a particular embodiment, the intermediate TFF may have a pore size of about 0.1 μm.

The source of cell-free culture medium 230 may take a variety of forms, including that of a system for prefiltration. Without limitation, the presently disclosed system may or may not include such a system for prefiltration. If employed, the prefiltration system is in communication with the MSC liquid culture and provides the cell-free culture medium. While one particular embodiment of a prefiltration system is shown and described with respect to FIG. 4B, prefiltration, if employed, may be implemented through a variety of techniques.

In addition, the presently disclosed system is not limited by the equipment required or process practiced to achieve the MSC liquid culture. For illustrative purposes, one such system and process is illustrated and discussed below with respect to FIG. 4A.

Various elements useful in implementing the presently disclosed system are also shown and described in illustrative embodiments. For example, feed vessels 230, 250 may be employed for providing fluid input to the first and second TFFs 236, 256. Various pumps 234, 238, 252, 260, 264 may also be employed to propel fluid throughout portions of the presently disclosed system. Further, a diafiltration reservoir 258 may provide a source of diafiltration buffer with respect to the second TFF, as will be shown and described with respect to FIG. 4D.

Figure 4A:
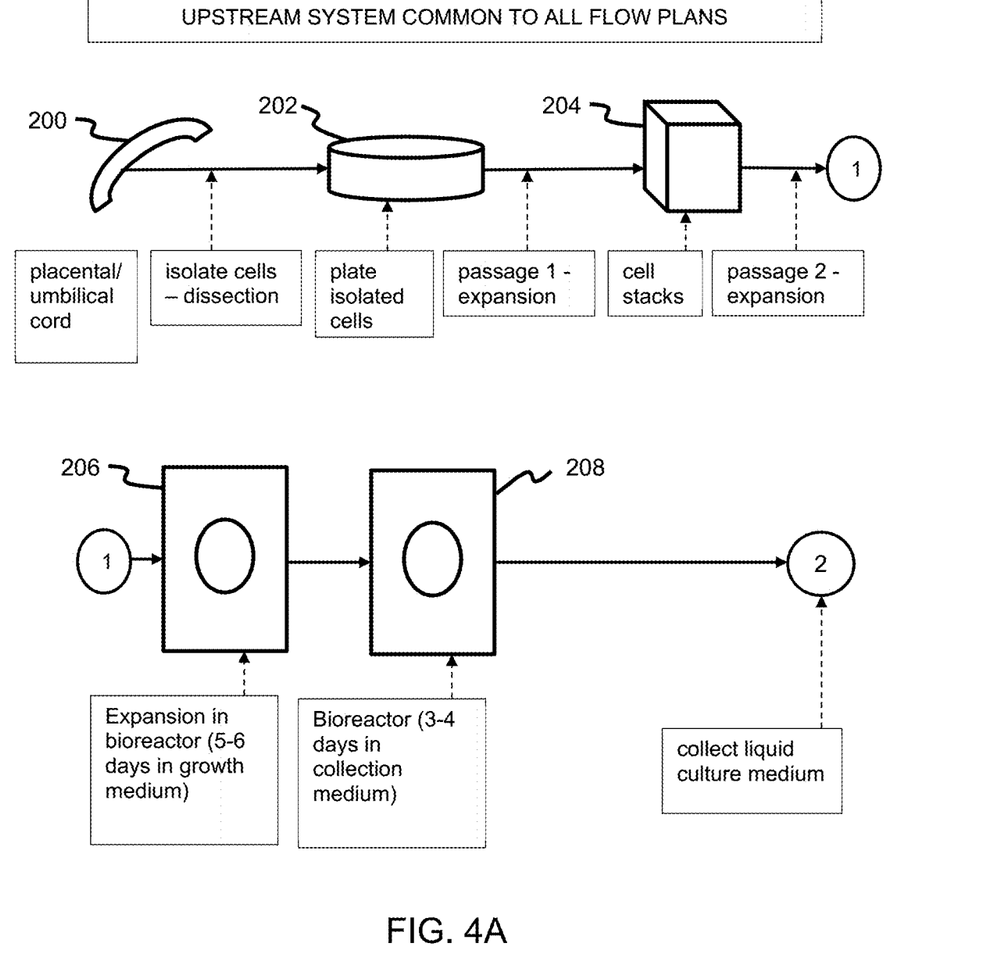
FIG. 4A is a diagrammatic representation of the upstream system which provides the liquid MSC culture.

With respect to FIG. 4A, an optional and illustrative system for obtaining a cell-free mesenchymal stem cell (MSC) liquid culture is described. Human placental and/or umbilical cord tissue 200 is processed according to known techniques in order to isolate MSCs, which are then plated 202. The cell culture is then harvested 204 prior to introduction into a suitable bioreactor 206. Cell culture expansion may be repeated as desired or required.

Cell culture expansion occurs in growth medium within the bioreactor 206 for a period of time. In an exemplary embodiment, this time period is five to six days. The cell culture may then be introduced into a subsequent bioreactor 208 containing collection medium for a period of time which, in an illustrative embodiment is three to four days. The MSC culture medium is then collected and processed for cell removal.

Figure 4B:
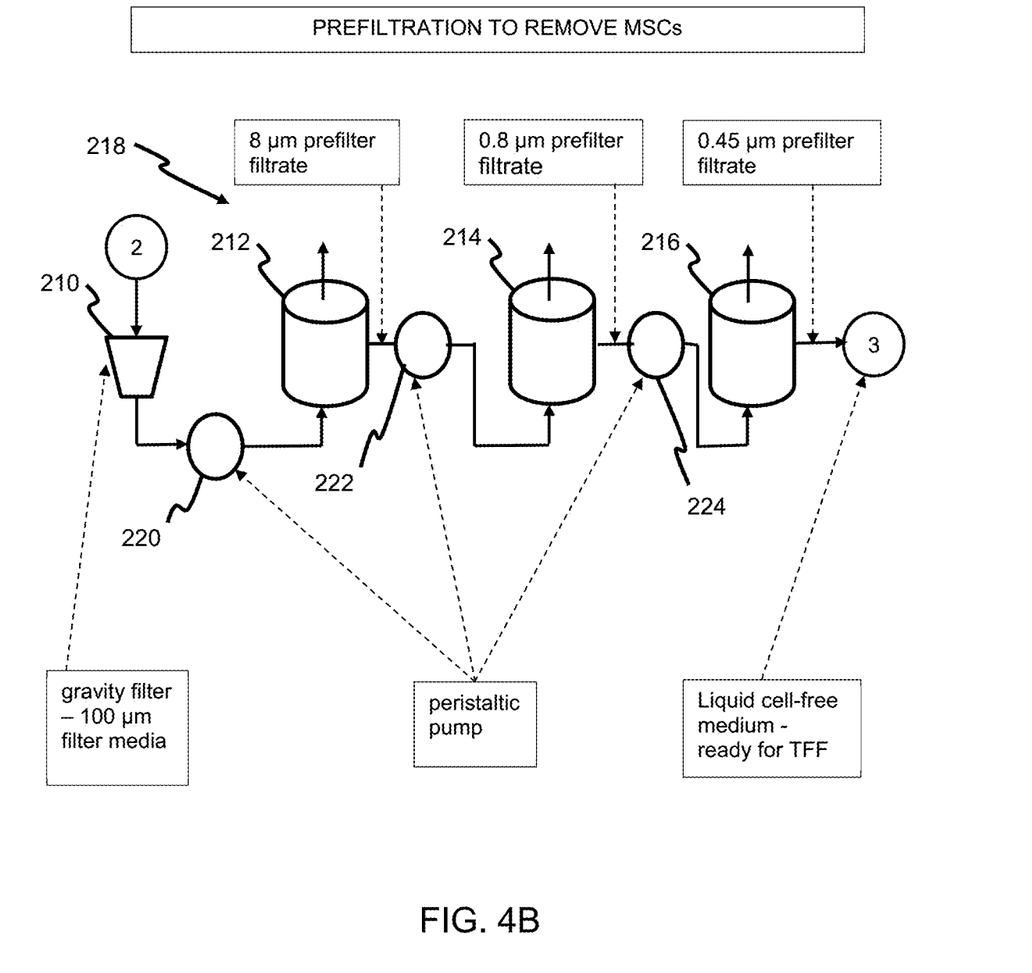
FIG. 4B is a diagrammatic representation of one embodiment of the system according to the disclosure for the removal of the MSCs to provide the source of cell-free culture medium.
Figure 4C:
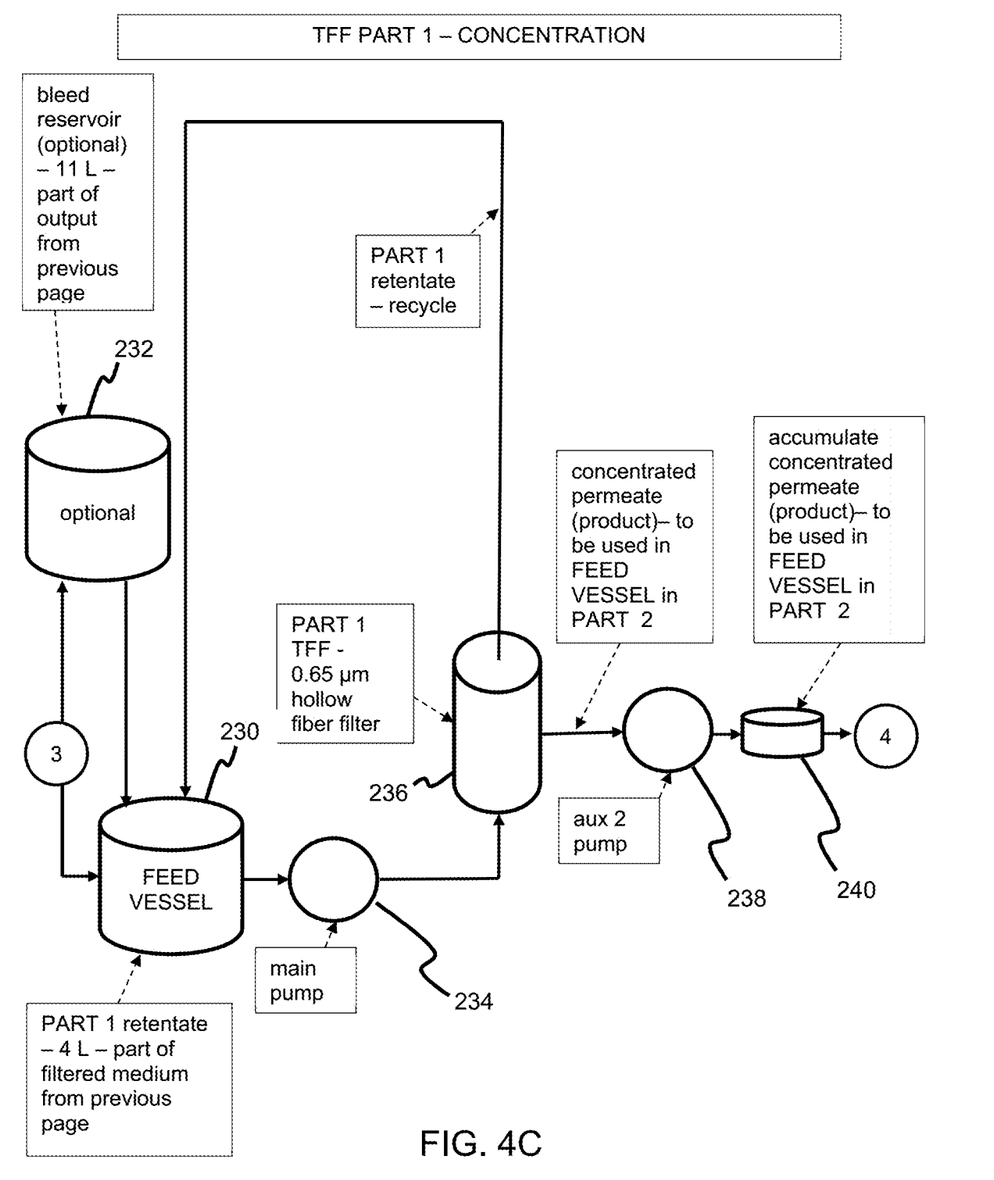
FIG. 4C is a diagrammatic representation of an embodiment of the first part of the tangential flow filtration system providing the permeate.
Figure 4D:
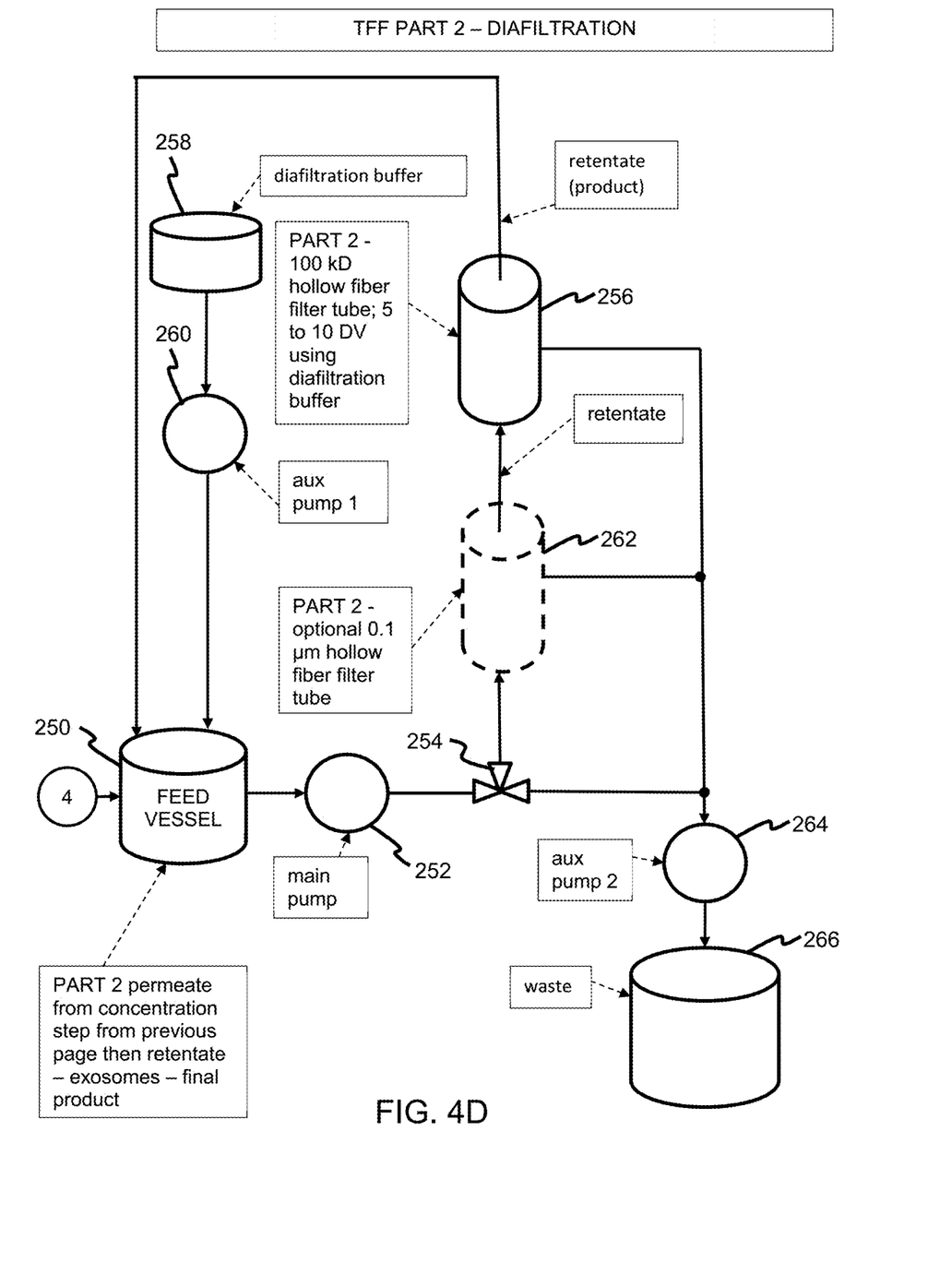
FIG. 4D is a diagrammatic representation of an embodiment of the diafiltration part of the tangential flow filtration system providing the exosomal retentate.

With respect to FIG. 4B, an optional and illustrative system for prefiltration of MSCs for cell removal is disclosed, though it is emphasized that a variety of prefiltration equipment may be utilized to achieve satisfactory cell removal results.

As illustrated, the culture introduced to an optional gravity filter 210 which, in the exemplary embodiment, contains 100 μm filtered media. Other pore sizes may be utilized, and other preliminary filtration techniques may also be practiced, as desired or as necessary.

Next, the MSC culture medium is passed through a prefilter module 218. As shown, the prefilter module is comprised of a sequence of discrete prefilters 212, 214, 216, each having a successively smaller filter pore size. The filtrate of an upstream prefilter is introduced into the subsequent prefilter in order to achieve an ultimate filtrate that is cell-free. Three prefilters are shown, though a different number may be utilized. Alternatively, the illustrated prefilters may be replaced with one or more additional gravity filters or with one or more centrifuge systems.

The prefilter(s) 212, 214, 216 may have a pore size of about 10.0 μm to 0.1 μm. For example, in the illustrated embodiment, the first prefilter 212 has a pore size of about 8.0 μm, the second prefilter 214 has a pore size of about 0.8 μm, and the third prefilter 216 has a pore size of about 0.45 μm. These prefilters may in one embodiment have filter media formed of polypropylene, and of polypropylene fleece, in particular.

One or more pumps 220, 222, 224 in association the prefilter module 218 may be used due to the small pore size required for cell removal. Thus, in the illustrated embodiment, there is one pump for pumping cell culture into each of the discrete prefilters. These pumps may be, for example, peristaltic pumps.

The cell-free filtered MSC medium is then introduced into a feed vessel 230. The feed vessel may be provided as a large container having a capacity of, for example, 15 liters. Alternatively, as shown in FIG. 4C, a smaller feed vessel 230 may be employed along with an auxiliary vessel 232, such as the illustrated bleed vessel. In the illustrated embodiment, the cell-free filtered MSC medium is distributed between these two vessels.

A pump 234 associated with the first feed vessel 230 is then utilized to initially pump the filtered cell-free MSC medium to the input of a first tangential flow filter (TFF) 236. In the illustrated embodiment, the first TFF is a hollow-fiber filter tube (HFT) TFF though other hollow fiber filter formats may be employed as with respect to the first TFF, other hollow fiber filter formats may be employed. The first HFT TFF has a pore size in the range of about 0.1 μm to about 1.0 μm. In one example, the first HFT TFF has a pore size of about 0.65 μm.

The permeate of the first TFF 236 is accumulated into a collection vessel 240 to form a source of concentrated product. As shown in FIG. 4B, an auxiliary pump 238 may be employed to accumulate the permeate of the first TFF.

Meanwhile, the retentate from the first TFF 236 is recycled into the first feed vessel 230. If an auxiliary feed vessel 232 is employed for collecting the filtered, cell-free MSC medium, the retentate may be mixed with additional filtered medium. The process of filtering the retentate or combination of retentate and filtered medium continues until a sufficient concentration of permeate has been collected in the collection vessel 240.

With respect to FIG. 4D, the concentrated product from the permeate of the first TFF is then provided to the input of a second TFF 256 via a second feed vessel 250. While illustrated as discrete containers in FIGS. 4B and 4C, the collection vessel 240 and the second feed vessel 250 may in one embodiment be the same vessel. The second TFF is another HFT TFF in the illustrated embodiment and has a pore size in the range of 30 kD to 600 kD. Specifically, in one embodiment, the second TFF has a pore size of about 100 kD. A pump 252 may be utilized for the purpose of providing the concentrated product from the second feed vessel to the input of the second TFF. This pump, as well as the pump 234 associated with the first feed vessel, may be a peristaltic pump in one non-limiting embodiment.

The permeate of the second TFF 256 is directed to a waste container 266 as the product in the retentate is again flowed through the second TFF via the second feed vessel 250. A diafiltration reservoir 258 is in fluid communication with the second feed vessel for enabling diafiltration through the second TFF. Diafiltration buffer, such as saline, selectively flows from the diafiltration reservoir into the second feed vessel, replacing the fluid that exits the second TFF as permeate. An auxiliary pump 260 may be utilized to selectively convey the diafiltration buffer into the second feed vessel. Such an auxiliary pump may be a peristaltic pump, for example, though other pump types may be employed.

In an embodiment, the diafiltration reservoir 258 volume is sufficient to retain a volume of diafiltration buffer that is five to ten times the volume of the accumulated, concentrated permeate from the first TFF 236. Thus, in this embodiment, the second TFF 256 retentate may be washed through five to ten diafiltration volumes (DVs). Other quantities of diafiltration buffer may be employed, however.

Once diafiltration is complete, the second TFF 256 retentate is again recycled to the second feed vessel 250 then back to the input of the second TFF until a desired degree of concentration of the desired exosome product has been achieved. The final product comprising concentrated exosomes is then collected in the second feed vessel. Fluid valves 254 may be utilized to redirect unwanted fluid into a suitable waste container 266 for collection. Another auxiliary pump 264 may be provided for the purpose of waste collection.

Optionally, a third TFF 262, which may be referred to as an intermediate TFF, may be disposed in fluid communication intermediate the second feed vessel 250 and associated second pump 252 and the second TFF 256. The intermediate TFF may be an HFT TFF and in one embodiment is provided with a pore size in the range of about 0.45 μm to about 2.0 μm. Specifically, in an exemplary embodiment, the intermediate TFF has a pore size of about 0.1 μm. The output from the second feed vessel 520 is in fluid communication with the input of the intermediate TFF, if used, via the respective pump. The permeate from the intermediate TFF is directed to a waste stream as the product in the retentate of the intermediate TFF is provided to the input of the second TFF, in this alternative embodiment. Diafiltration and concentration, as previously described, thus takes place within the intermediate TFF as well, if used.

The hollow fiber filter tubes of one or more of the first, second, and intermediate TFFs 236, 256, 262 may be provided as polysulfane, polysulfone, and/or modified polysulfone.

Figure 1:
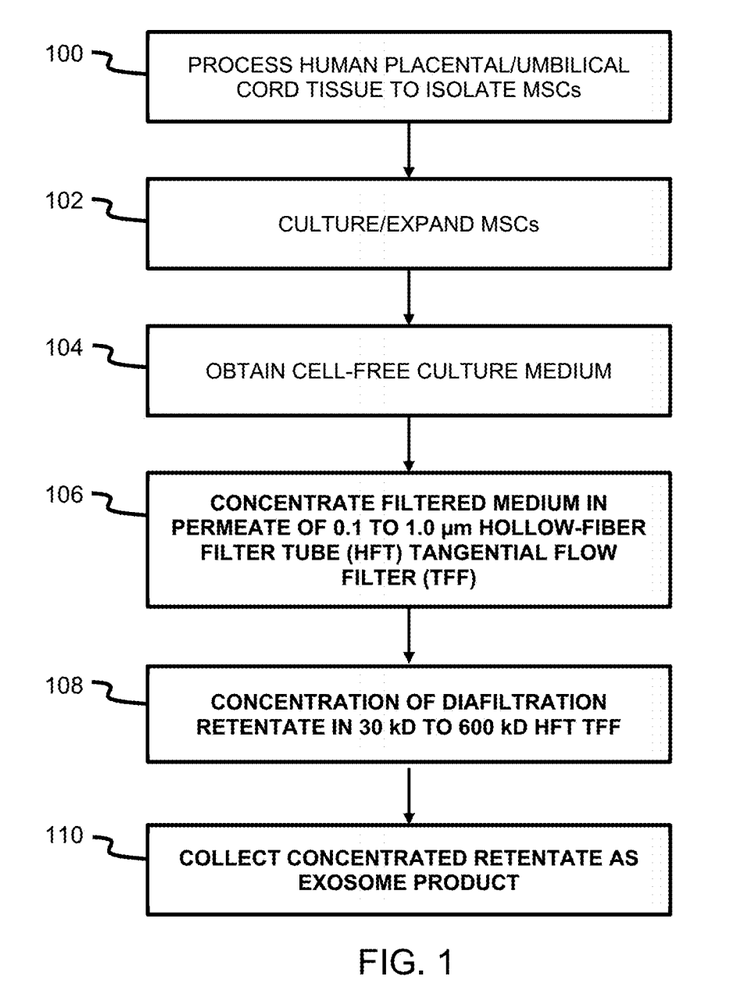
FIG. 1 is a flow chart delineating the steps (bolded) of the method according to one embodiment of the disclosure.
Figure 2A:
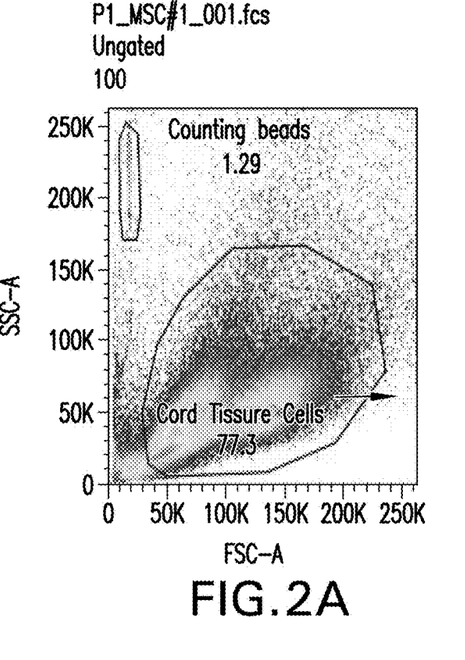
FIG. 2A is a representation of a flow cytometry plot of control MSCs (control)
Figure 2B:
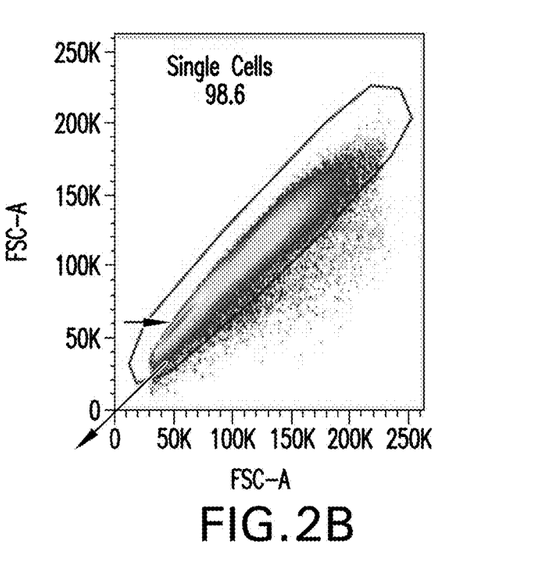
FIG. 2B is a representation of a flow cytometry plot of single MSCs from an umbilical cord tissue.
Figure 2C:
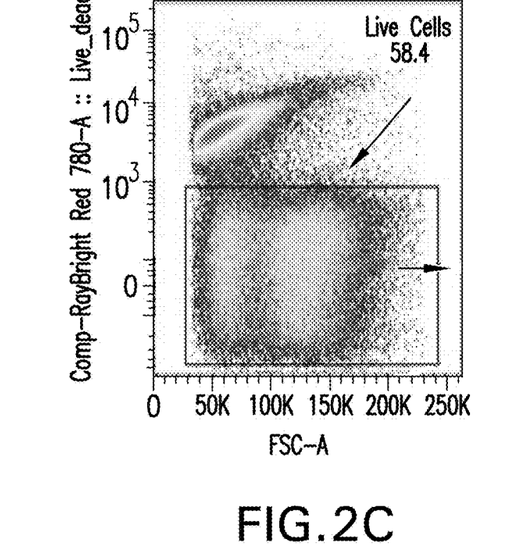
FIG. 2C is a representation of a flow cytometry plot of live MSCs from umbilical cord.
Figure 2D:
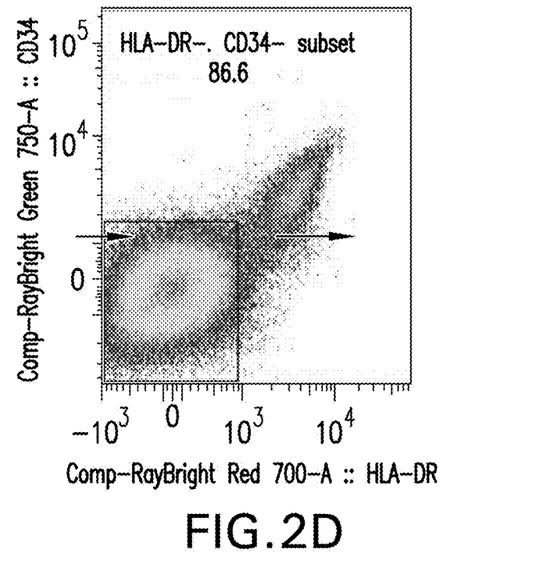
FIG. 2D is a representation of a flow cytometry plot of a subset of umbilical cord MSCs expressing HLA-DR and CD34.
Figure 2E:
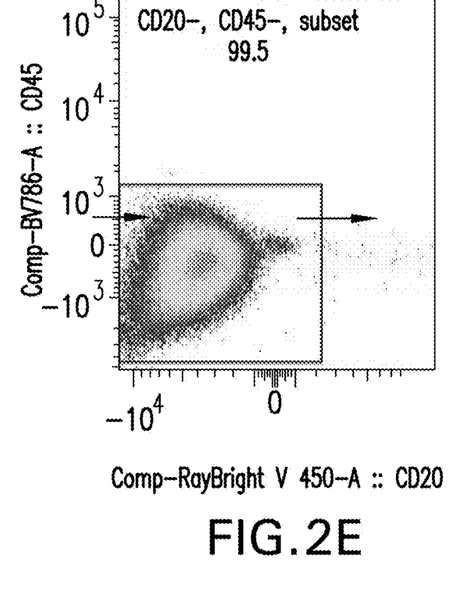
FIG. 2E is a representation of a flow cytometry plot of a subset of CD20 and CD45-expressing MSCs from umbilical cord.
Figure 2F:
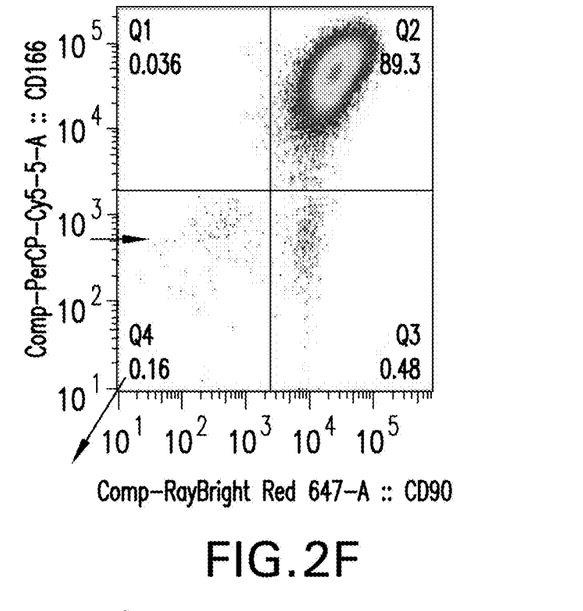
FIG. 2F is a representation of a flow cytometry plot of a subset of umbilical cord MSCs expressing CD90.
Figure 2G:
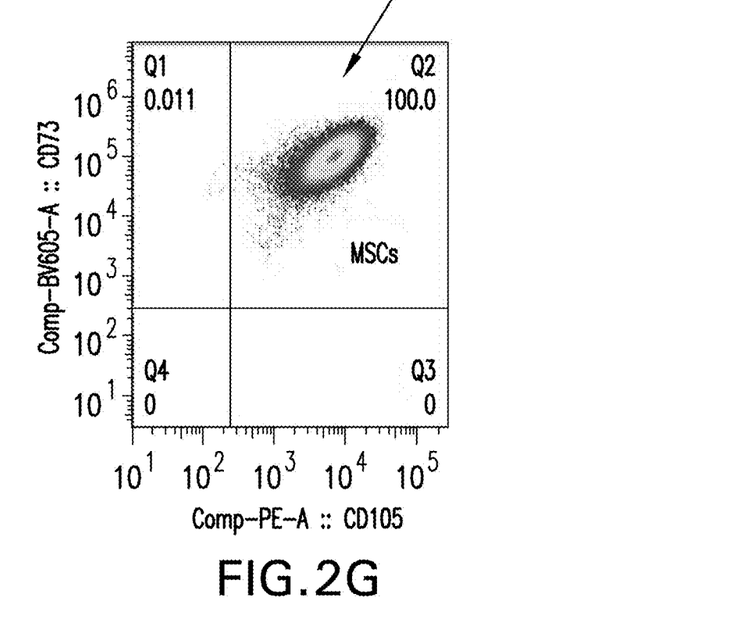
FIG. 2G is a representation of a flow cytometry plot of CD105-expressing cells from an umbilical cord sample.
Figure 3A:
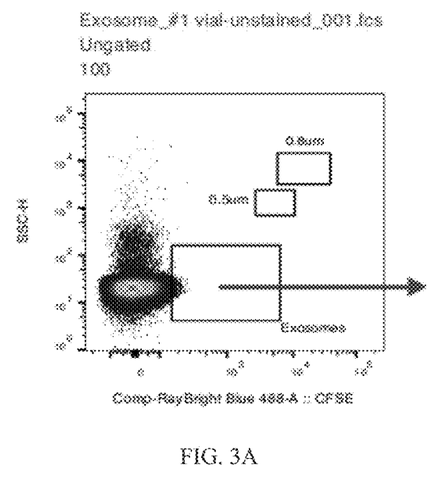
FIG. 3A is a representation of a flow cytometric plot of a sample of umbilical cord MSCs.
Figure 3B:
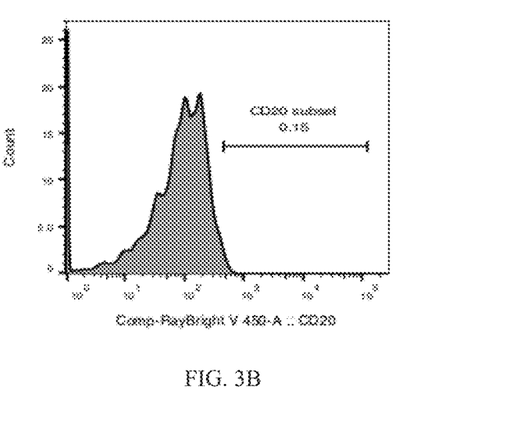
FIG. 3B is a graphic representation of counts reflecting the presence of CD20-expressing exosomes from the MSC sample shown in FIG. 3A.
Figure 3C:
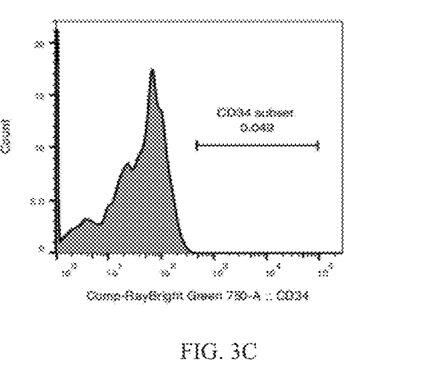
FIG. 3C is a graphic representation of counts reflecting the presence of CD34-expressing exosomes from the MSC sample in FIG. 3A.
Figure 3D:
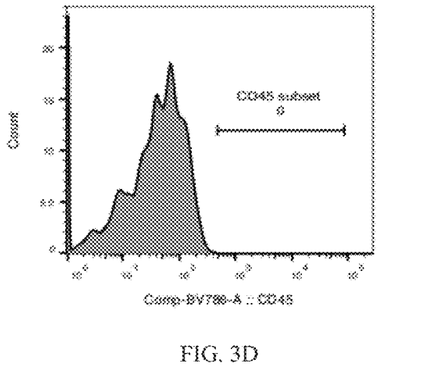
FIG. 3D is a graphic representation of counts reflecting the presence of CD45-expressing exosomes from the MSC sample in FIG. 3A.
Figure 3E:
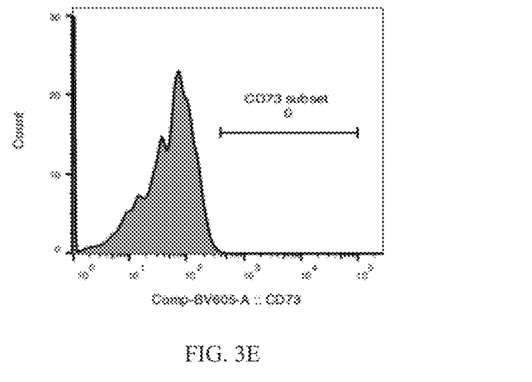
FIG. 3E is a graphic representation of the counts reflecting the presence of CD73-expressing exosomes from the MSC sample in FIG. 3A.
Figure 3F:
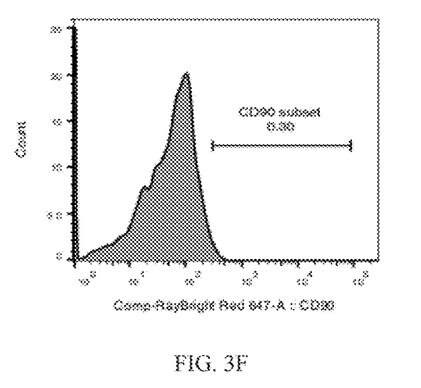
FIG. 3F is a graphic representation of counts reflecting the presence of CD90-expressing exosomes from the MSC sample in FIG. 3A.
Figure 3G:
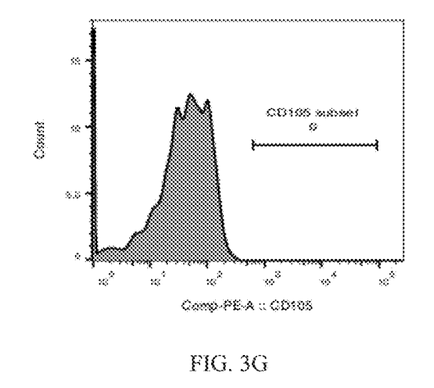
FIG. 3G is a graphic representation of counts reflecting the presence of CD105-expressing exosomes from the MSC sample in FIG. 3A.
Figure 3H:
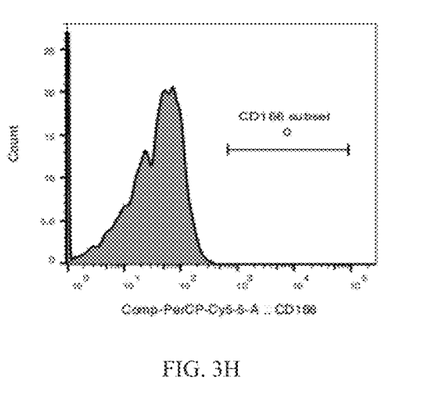
FIG. 3H is a graphic representation of counts reflecting the presence of CD166-expressing exosomes from the MSC sample in FIG. 3A.
Figure 3I:
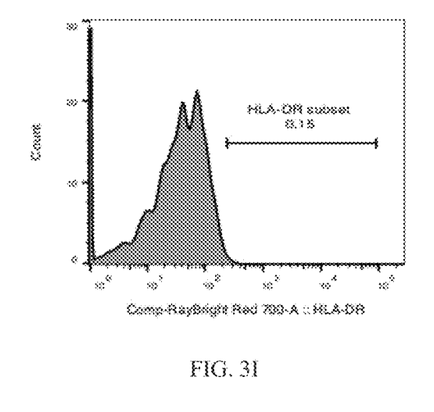
FIG. 3I is a graphic representation of counts reflecting the presence of HLA-DR-expressing exosomes from the MSC sample in FIG. 3A.

A simplified flow chart of the steps involved in utilizing the system of FIGS. 4A-4D is provided in FIG. 1. It is understood that this simplified flow chart may not explicitly list every step useful for obtaining an exosome product. For example, the simplified chart does not address use of an intermediate HFT TFF, as discussed above.

In a first step 100, human placental and/or umbilical cord tissue is processed in order to isolate mesenchymal stem cells (MSCs). The MSCs are then cultured and expanded 102, and a cell-free MSC culture medium is obtained therefrom 104, such as through the use of a prefilter module as previously described.

The filtered cell-free culture medium is then concentrated 106 in the permeate of an about 0.1 μm to about 1.0 μm first hollow-fiber filter tube (HFT) tangential flow filter (TFF). This permeate is the conveyed to an about 30 kD to about 600 kD or an about 60 kD to about 150 kD second HFT TFF, where a source of diafiltration buffer enables, for example, a 5 DV to 10 DV diafiltration process 108. Subsequently, the retentate of the second TFF is concentrated to a desired degree and the concentrated retentate is then collected 110 as the final exosome product.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A system for the production of a plurality of exosomes, comprising:
a source of liquid cell-free culture medium from a liquid mesenchymal stem cell (MSC) culture;

a first tangential flow filter (TFF) for separating the cell-free culture medium into a first permeate and a first retentate; and an intermediate TFF in fluid communication with, and between, the first TFF and a second TFF, wherein an input of the intermediate TFF is the first permeate, for separating an intermediate permeate and an intermediate retentate output, and wherein an input of the second TFF is the intermediate retentate for separating the intermediate retentate into a second permeate and a second retentate, wherein the second retentate comprises the plurality of exosomes.

2. The system of claim 1, wherein the first TFF is a hollow fiber filter having a pore size of about 0.1 µm to about 1.0 µm.

3. The system of claim 1, wherein the second TFF is a hollow fiber filter having a pore size of about 30 kD to about 600 kD.

4. The system of claim 3, wherein the second TFF is a hollow fiber filter having a pore size of about 50 kD to about 150 kD.

5. The system of claim 1, wherein the first TFF has a pore size of about 0.65 µm.

6. The system of claim 1, wherein the second TFF has a pore size of about 100 kD.

7. The system of claim 1, wherein the intermediate TFF has a pore size of about 0.45 µm to about 2.0 µm.

8. The system of claim 7, wherein the intermediate TFF has a pore size of about 0.1 µm.

9. The system of claim 1, wherein the first and second TFFs are comprised of polysulfane, polysulfone, and/or modified polysulfone.

10. The system of claim 1, further comprising a prefilter module through which the liquid MSC culture medium is passed to obtain the source of liquid, cell-free MSC culture medium.

11. The system of claim 10, wherein the prefilter module pore size is between about 10.0 µm and about 0.1 µm.

12. The system of claim 10, wherein the prefilter module comprises a sequence of plural, discrete prefilters, each having a successively smaller filter pore size.

13. The system of claim 12, wherein the plural discrete prefilters each comprise a polypropylene.

14. The system of claim 12, wherein the sequence of plural discrete filters is comprised of three successive discrete prefilters having pore sizes of about 8.0 µm, about 0.8 µm, and about 0.45 µm, respectively.

15. The system of claim 10, further comprising a first feed vessel in fluid communication with the prefilter module and the first TFF.

16. The system of claim 1, further comprising a first feed vessel in fluid communication with the liquid, cell-free culture medium source and the first TFF, the first feed vessel configured to receive the liquid, cell-free culture medium and to provide the liquid, cell-free culture medium to the first TFF.

17. The system of claim 16, wherein the first feed vessel is further configured to receive the retentate from a retentate output of the first TFF and to return the retentate from the first TFF to an input of the first TFF.

18. The system of claim 16, further comprising a first pump intermediate the first feed vessel and the first TFF for selectively pumping the contents of the first feed vessel to an input of the first TFF.

19. The system of claim 1, further comprising a second feed vessel in fluid communication with a permeate output of the first TFF and an input of the intermediate TFF, the second feed vessel configured to receive permeate from a permeate output of the first TFF and to provide the permeate output of the first TFF to an input of the intermediate TFF.

20. The system of claim 19, further comprising a second pump intermediate and in fluid communication with the permeate output of the first TFF and the second feed vessel for selectively pumping the permeate of the first TFF to the second feed vessel.

21. The system of claim 19, further comprising a third pump intermediate and in fluid communication with the second feed vessel and the input of the intermediate TFF for selectively pumping the contents of the second feed vessel to an input of the intermediate TFF.

22. The system of claim 19, wherein the second feed vessel is configured to receive a retentate from a retentate output of the second TFF and to return the retentate from the second TFF to the input of the intermediate TFF.

23. The system of claim 22, further comprising a diafiltration reservoir in fluid communication with the second feed vessel for providing a supply of diafiltration buffer thereto, whereby the second feed vessel is configured to provide diafiltration buffer to the input of the intermediate TFF and the second TFF.

24. The system of claim 23, further comprising a fourth pump intermediate and in fluid communication with the diafiltration reservoir and the second feed vessel for selectively pumping the contents of the diafiltration reservoir to the second feed vessel.

25. The system of claim 1, further comprising a product reservoir in fluid communication with a retentate output of the second TFF for selectively receiving the second retentate therefrom.

26. A method of isolating a plurality of substantially undamaged exosomes from a liquid culture of mesenchymal stem cells (MSCs), comprising:
removing the MSCs from the liquid culture to obtain a liquid cell-free culture medium; and
isolating the plurality of exosomes from the liquid cell-free culture medium by tangential flow filtration using a system of claim 1.

27. The method of claim 26, wherein the plurality of exosomes is isolated from the liquid cell-free culture medium by tangential flow filtration, by:
filtering the liquid cell-free culture medium through a first hollow fiber filter having a pore size of about 0.1 µm to about 1.0 µm to obtain a first permeate; and
subjecting the first permeate to diafiltration through a second hollow fiber filter having a pore size of about 30 kD to 600 kD to obtain a retentate.

28. The method of claim 27, wherein the first hollow fiber filter has a pore size of about 0.65 µm.

29. The method of claim 27, wherein the second hollow fiber filter has a pore size of about 50 kD to about 150 kD.

30. The method of claim 27, wherein the second hollow fiber filter has a pore size of about 100 kD.

31. The method of claim 27, further comprising filtering the first permeate through an intermediate hollow fiber filter having a pore size of about 0.45 µm to about 2.0 µm to obtain a second permeate, and then filtering the second permeate through the second hollow fiber to obtain the permeate.

32. The method of claim 31, wherein the intermediate hollow fiber filter has a pore size of about 0.1 µm.

33. The method of claim 27, wherein the hollow fiber filter comprises polysulfane, polysulfone, and/or modified polysulfone.

34. The method of claim 26, wherein the MSC culture is obtained from human placental and/or umbilical cord tissue.

35. The method of claim 26, wherein the MSCs are removed from the liquid MSC culture by gravity filtration.

36. The method of claim 35, wherein the MSCs are removed by filtration through a prefilter having a pore size of at least about 0.4 µm.

37. The method of claim 36, wherein the prefilter comprise polypropylene.

38. The method of claim 27, wherein the retentate consists essentially of a plurality of exosomes.

39. The method of claim 26 or claim 27, wherein about 32 trillion to about 50 trillion exosomes are obtained from a culture of about 7 billion to about 10 billion mesenchymal stem cells.

* * * * *